United States Patent [19]

Vallin et al.

[11] Patent Number: 4,547,441

[45] Date of Patent: Oct. 15, 1985

[54] ELECTROCHEMICAL CELL WITH NEGATIVE ACTIVE MATERIAL BASED ON AN ALKALI OR ALKALINE EARTH METAL

[75] Inventors: Didier Vallin, Ligugé; Jean-Yves Grassien, La Villedieu du Clain; Philippe Chenebault; Alain Kerouanton, both of Poitiers, all of France

[73] Assignee: Saft, Romainville, France

[21] Appl. No.: 687,179

[22] Filed: Dec. 28, 1984

[30] Foreign Application Priority Data

Dec. 3, 1984 [FR] France .............................. 84 18399

[51] Int. Cl.⁴ ............................................. H01M 6/14
[52] U.S. Cl. ................................... 429/196; 429/197; 429/199
[58] Field of Search ............... 429/196, 197, 199, 194, 429/102

[56] References Cited

U.S. PATENT DOCUMENTS 4,228,229  10/1980  Gabano et al. ...................... 429/196
4,309,490   1/1982  Chua et al. ......................... 429/101
4,375,502   3/1983  Gabano .......................... 429/197 X Primary Examiner—Anthony Skapars
Attorney, Agent, or Firm—Kenyon & Kenyon

[57] ABSTRACT

In an electrochemical cell the negative active material is an alkali or alkaline earth metal, such as lithium, and the electrolyte comprises a solute and at least one solvent selected from the liquid oxyhalides and which serves also as the positive active material. The electrolyte further comprises a mineral substance the effect of which is to significantly reduce the voltage rise delay of the cell.

11 Claims, 1 Drawing Figure

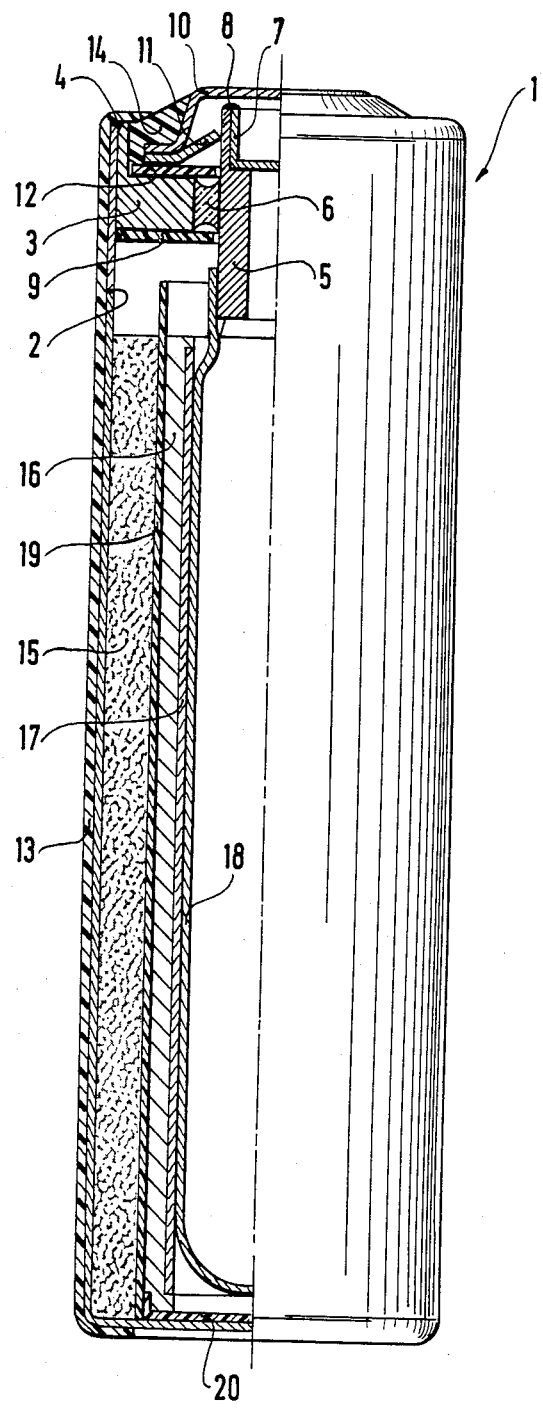

ELECTROCHEMICAL CELL WITH NEGATIVE ACTIVE MATERIAL BASED ON AN ALKALI OR ALKALINE EARTH METAL

BACKGROUND OF THE INVENTION

1. Field of the Invention

The present invention concerns an electrochemical cell in which the negative active material is based on an alkali or alkaline earth metal and the positive material is a liquid oxyhalide such as thionyl chloride and also constitutes the electrolyte solvent, the electrolyte possibly comprising other cosolvents.

2. Description of the Prior Art

When a cell of this kind is not being discharged, the liquid substance serving as the positive material and electrolyte solvent reacts with the metal of the negative electrode as a result of which a protective surface film is formed on this electrode. The presence of a film of this kind constitutes a disadvantage since it may cause a "voltage rise delay" at the start of discharge; in other words, the normal operating voltage is not obtained until the end of a certain time delay. This phemonenon is more accentuated with longer storage times and higher storage temperatures.

Various solutions have already been put forward to minimize this "voltage rise delay".

For example, U.S. Pat. No. 4,309,940 published Jan. 5, 1982 describes a lithium-thionyl chloride cell of which the electrolyte solute is a complex salt resulting from the action of lithium chloride LiCl on aluminum chloride $AlCl_3$, the latter being totally neutralized by LiCl to form $LiClCl_4$. The patent provides for the addition to the electrolyte of a certain quantity of sulfur dioxide $SO_2$, the molar ratio of $AlCl_3:SO_2$ being between 0.9 and 1.5:1. Thus this method entails the addition of significant concentrations of sulfur dioxide, which may result in cell pressurization phenomena and practical difficulties of implementation.

There are proposed in U.S. Pat. No. 4,228,229 published Oct. 14, 1980 and French Pat. No. 2 485 271 published Dec. 24, 1981 other techniques employing partial or total neutralization of solutions of aluminum chloride by Lewis bases other than LiCl, $Li_2O$ or $Li_2CO_3$, for example. These techniques have made it possible to achieve a significant improvement as compared with the initial electrolyte prepared by neutralization of a solution of $AlCl_3$ with LiCl. They produce solutions also containing sulfur dioxide $SO_2$. In this case, it is generated "in situ" during the neutralization of $AlCl_3$ by the corresponding Lewis bases, but in proportions such that the molar ratio of $AlCl_3:SO_2$ is greater than or equal to 2:1, acording to the degree of neutralization selected.

To give an example, and for reasons associated with cell self-discharge, use has been made of totally neutralized electrolyte (molar ratio of $AlCl_3:SO_2=2:1$) with a concentration of $LiAlCl_4$ corresponding to 1.35 moles/l. The reaction used is, for example, as follows:

$$2AlCl_3 + Li_2O + SOCl_2 \rightarrow 2LiAlCl_4 + SO_2$$

Although the solution explained hereinabove has resulted in significant improvements in terms of reduced voltage rise delays, it has nevertheless proven insufficient for a certain number of applications. An object of the present invention is to further reduce the voltage rise delay.

SUMMARY OF THE INVENTION

The invention consists in an electrochemical cell comprising a negative active material based on an alkali or alkaline earth metal and an electrolyte containing a solute, at least one solvent selected from the group comprising the liquid oxyhalides and also constituting the positive active material and at least one mineral substance of the alkali or alkaline earth polyhalogenosulfatometallate type having the formula $MM'_m(SO_3X)_n$ in which M is said alkali or alkaline earth metal, M′ is selected from the group comprising Al, B, Ga, In, V, Sb, Nb, Si, W and Ta, and X is selected from the group comprising chlorine, fluorine, bromine and iodine.

The concentration of the mineral substance is greater than 0.01% by weight of electrolyte.

In a particularly advantageous embodiment, the negative active material is based on lithium and said solvent is thionyl chloride $SOCl_2$; the solute is $LiAlCl$ and the mineral substance has the formula $LiAl(SO_3Cl)_4$.

In one variant, the negative active material is based on sodium and said solvent is thionyl chloride; said solute is $NaAlCl_4$ and said mineral substance has the formula $NaAl(SO_3Cl)_4$.

The negative active material may also be based on calcium, magnesium or potassium.

The oxyhalide may instead be phosphoryl chloride $POCl_3$, vanadyl trichloride $VOCl_3$, vanadyl tribromide $VOBr_3$, thionyl bromide $SOBr_2$, sulfuryl chloride $SO_2Cl_2$, chromyl chloride $CrO_2Cl_2$ or selenium oxychloride $SeOCl_2$ or mixtures thereof.

The electrolyte preferably further contains dissolved sulfur dioxide.

The mineral substance may be added directly to the electrolyte or obtained in situ by reacting the electrolyte with a substance selected from the group comprising $HSO_3X$, $SO_3$, $H_2SO_4$ and mixtures thereof, X being selected from the group comprising chlorine, fluorine, bromine and iodine.

Other objects and advantages will appear from the following description of examples of the invention, when considered in connection with the accompanying drawing, which is a schematic representation of a cell in accordance with the invention as seen in cross-section, and the novel features will be particularly pointed out in the appended claims.

BRIEF DESCRIPTION OF THE DRAWING

The FIGURE is an embodiment of a cell in accordance with the invention.

DESCRIPTION OF THE PREFERRED EMBODIMENTS

A number of series of cells of the type shown in the FIGURE have been made. These cells, of cylindrical shape, have the following dimensions: height=50 mm, outside diameter=13.4 mm.

The cell 1 as illustrated comprises a can 2 of a composite sheet material consisting of a sheet of stainless steel and a sheet of nickel laminated together, the nickel sheet being on the inside. The closure of the can comprises a stainless steel ring 3 welded at 4 to the edge of the can and electrically insulated from a ferro-nickel alloy cylinder 5 by a glass seal 6. The cylinder 5 is closed by a ferro-nickel alloy plug 7 which is welded to it at 8. A polytetrafluorethylene disk 9 protects the ring 3 against chemical attack by the constituents of the cell.

Thus the cell is hermetically sealed. It is terminated externally by a stainless steel cap 10 which overlies the cylinder 5 and is in contact with a ring 11 which is a force fit over the cylinder 5. The ring 11 is insulated from the ring 3 by a polytetrafluoroethylene ring 12.

The can is covered with a polyvinyl chloride sheath 13 and the edges of the cap 10 are protected by a heat-hardenable resin 14.

The cathode collector 15 is a porous cylinder consisting of a mixture of 85% acetylene black with 15% polytetrafluorethylene in contact with the can 2. The anode 16 consists of lithium foil wound onto the anode collector 17, itself consisting of a wound stainless steel foil. A stainless steel spring 18 urges the anode towards the cathode collector 15 from which it is separated by a separator 19. The polytetrafluorethylene disk 20 insulates the anode from the bottom of the can 2. The spring 18 is welded to the cylinder 15 so that the cap 10 constitutes the negative terminal of the cell, the positive terminal of which consists of the bottom of the can 2 not protected by the sheath 13. The anode surface area facing the cathode collector is 10 cm².

Various types of solution serving simultaneously as electrolyte and positive active materials have been placed in the device.

EXAMPLES

Electrolyte A—This is a prior art electrolyte. A solution of aluminum chloride $AlCl_3$ is neutralized in thionyl chloride by the Lewis base LiCl; $LiAlCl_4$ is obtained (concentration 1.35 moles/l).

Electrolyte B—This is also a prior art electrolyte. It is obtained by neutralizing a solution of $AlCl_3$ in thionyl chloride using the Lewis base $Li_2CO_3$. The reaction is as follows:

$$Li_2CO_3 + 2AlCl_3 + SOCl_2 \rightarrow 2LiAlCl_4 + SO_2 + CO_2$$

The concentration of $LiAlCl_4$ is 1.35 moles/l.

Electrolyte C (in accordance with the invention)—There is added to electrolyte A 0.5% by weight of electrolyte of lithium tetrachlorosulfatoaluminate $LiAl(SO_3Cl)_4$.

Electrolytes $D_1$, $D_2$, $D_3$ (in accordance with the invention)—These electrolytes consist of electrolyte B and, respectively, 0.1%, 0.5%, 1% of $LiAl(SO_3Cl)_4$.

Electrolytes $E_1$, $E_2$ (in accordance with the invention)—There is added to electrolyte B respectively 0.1%, 0.5% by weight of electrolyte of sulfur dioxide $SO_2$. In the presence of $LiAlCl_4$, the sulfur dioxide results in the synthesis of $LiAl(SO_3Cl)_4$ by the reaction:

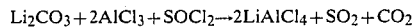

$$LiAlCl_4 + 4SO_3 \xrightarrow{SOCl_2} LiAl(SO_3Cl)_4$$

Electrolyte F (in accordance with the invention)—There is added to electrolyte B 0.5% of commercially available chlorosulfonic acid $HSO_3Cl$ which produces the following reaction:

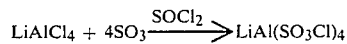

$$LiAlCl_4 + 4HSO_3Cl \rightarrow LiAl(SO_3Cl)_4 + 4HCl$$

The hydrochloric acid thus formed may easily be eliminated by reflow heating for a few hours.

Electrolyte G (in accordance with the invention)—There is added to electrolyte B 0.5% of chlorosulfonic acid $HSO_3Cl$ and 0.5% of sulfur dioxide. In this way there were obtained ten series of cells A, B, C, $D_1$, $D_2$, $D_3$, $E_1$, $E_2$, F and G which were stored for seven days at ambient temperature and then kept at 70° C. for seven days. 24 hours after removal from the oven the following tests were carried out:

measurement of the impedance Z (in ohms) at 40 Hz, discharge at ambient temperature through a 50 ohms resistor (current density of substantially 5 mA/cm²), the voltage U at the cell terminals being measured 0.3 s, 5 s and 60 s after initiating discharge.

The average results obtained are listed in the table below.

| Cell | emf (V) | Z (ohms) | U at 0.3 s (V) | U at 5 s (V) | U at 60 s (V) |
| --- | --- | --- | --- | --- | --- |
| A | 3.706 | 825 | 1.48 | 2.12 | 2.80 |
| B | 3.705 | 345 | 2.29 | 2.77 | 2.92 |
| C | 3.706 | 329 | 2.37 | 2.68 | 2.92 |
| $D_1$ | 3.725 | 270 | 2.68 | 2.86 | 2.77 |
| $D_2$ | 3.709 | 104 | 2.85 | 3.31 | 3.32 |
| $D_3$ | 3.698 | 69.5 | 3.02 | 3.21 | 3.31 |
| $E_1$ | 3.708 | 305 | 2.39 | 2.44 | 2.50 |
| $E_2$ | 3.713 | 365 | 2.52 | 2.63 | 2.93 |
| F | 3.712 | 99 | 3.17 | 3.36 | 3.33 |
| G | 3.743 | 96 | 3.16 | 3.27 | 3.25 |

The improvement afforded by the invention is clearly shown in this table.

It will be understood that the quantities of mineral substance have been given by way of example only, the quantity of this substance being subject to variation from 0.01% up to saturation level in the electrolyte.

In one variant the lithium may be replaced with sodium; the solute is then advantageously $NaAlCl_4$ and the mineral substance may be $NaAl(SO_3Cl)_4$. It may equally well be replaced by calcium or potassium, however.

In other embodiments employing a lithium anode, the solutes may have the following formlae: $LiBCl_4$, $LiGaCl_4$, $LiInCl_4$, $LiVCl_4$, $LiSiCl_5$, $LiSbCl_6$, $LiNbCl_6$, $LiTaCl_6$, $LiWCl_7$.

In the formulae for the additional mineral substances and solutes, chlorine may be replaced with fluorine, bromine or iodine.

It will be understood that various changes in the details, materials and arrangements of parts which have been herein described and illustrated in order to explain the nature of the invention may be made by those skilled in the art within the principle and scope of the invention as expressed in the appended claims.

There is claimed:

1. Electrochemical cell comprising a negative active material based on an alkali or alkaline earth metal and an electrolyte containing a solute and at least one solvent selected from the group consisting of the liquid oxyhalides, the electrolyte also constituting the positive active material and containing at least one mineral substance selected from the group consisting of the alkali or alkaline earth polyhalogenosulfatometallate having the formula $MM'_m(SO_3X)_n$ in which M is said alkali or alkaline earth metal, M' is selected from the group consisting of Al, B, Ga, In, V, Sb, Nb, Si, W and Ta, and X is selected from the group consisting of chlorine, fluorine, bromine and iodine.

2. Cell according to claim 1, wherein the concentration of said mineral substance is greater than 0.01% by weight of electrolyte.

3. Cell according to claim 1, wherein said electrolyte further contains sulfur dioxide.

4. Cell according to claim 1, wherein said liquid oxyhalide is thionyl chloride, said alkali metal is lithium and said solute has the formula $LiM'Cl_x$.

5. Cell according to claim 4, wherein the solute of said electrolyte is lithium tetrachloroaluminate with the formula $LiAlCl_4$.

6. Cell according to claim 5, wherein said mineral substance is a lithium tetrachlorosulfatoaluminate with the formula $LiAl(SO_3Cl)_4$.

7. Cell according to claim 4, wherein said electrolyte further comprises sulfur dioxide and the molar ratio of $M':SO_2$ is greater than 1.5:1.

8. Cell according to claim 1, wherein said liquid oxyhalide is thionyl chloride, said alkali metal is sodium and said solute is sodium tetrachloroaluminate with the formula $NaAlCl_4$.

9. Cell according to claim 8, wherein said mineral substance is sodium chlorosulfatoaluminate with the formula $NaAl(SO_3Cl)_4$.

10. Cell according to clam 1, wherein said mineral substance is added directly to said electrolyte.

11. Cell according to claim 1, wherein said mineral substance is formed in situ by reacting said electrolyte with a substance selected from the group consisting of $HSO_3X$, $SO_3$, $H_2SO_4$ and mixtures thereof, X being selected from the group consisting of chlorine, fluorine, bromine and iodine.

* * * * *